United States Patent
Garito et al.

(10) Patent No.: US 7,875,026 B1
(45) Date of Patent: Jan. 25, 2011

(54) FINGER-CONTROLLABLE ELECTROSURGICAL HANDPIECE

(75) Inventors: Jon C. Garito, Oceanside, NY (US); Alan G. Ellman, Oceanside, NY (US)

(73) Assignee: Ellman International, Inc. NY (US)

( * ) Notice: Subject to any disclaimer, the term of this patent is extended or adjusted under 35 U.S.C. 154(b) by 945 days.

(21) Appl. No.: 11/709,644

(22) Filed: Feb. 23, 2007

(51) Int. Cl.
*A61B 18/18* (2006.01)
(52) U.S. Cl. .............................. 606/41; 606/45; 606/49
(58) Field of Classification Search .............. 606/41–50
See application file for complete search history.

(56) References Cited

U.S. PATENT DOCUMENTS

| | | | | |
|---|---|---|---|---|
| 3,730,188 | A * | 5/1973 | Ellman | 606/37 |
| 3,920,022 | A * | 11/1975 | Pastor | 606/41 |
| 4,137,919 | A * | 2/1979 | Farin et al. | 606/51 |
| 4,834,095 | A * | 5/1989 | Miller | 606/45 |
| 5,196,007 | A * | 3/1993 | Ellman et al. | 606/32 |
| 5,224,947 | A * | 7/1993 | Cooper et al. | 606/123 |
| 5,685,878 | A * | 11/1997 | Falwell et al. | 606/49 |
| 5,984,918 | A * | 11/1999 | Garito et al. | 606/41 |
| 6,368,324 | B1 * | 4/2002 | Dinger et al. | 606/85 |
| 2003/0050634 | A1 * | 3/2003 | Ellman et al. | 606/41 |
| 2003/0139753 | A1 * | 7/2003 | Wang et al. | 606/139 |
| 2005/0267465 | A1 * | 12/2005 | Hillier et al. | 606/41 |

* cited by examiner

*Primary Examiner*—Linda C Dvorak
*Assistant Examiner*—Benjamin Lee

(57) ABSTRACT

An electrosurgical handpiece comprises a handle, a nose piece for threaded engagement with the handle at a first end for cooperating with a collet to grip an electrode, and a detachable cable connector at the opposite second end, the latter being characterized by a rotatable connection such that when the handle is rotated by the user, the cable will maintain its rotary position and thus not encumber rotation of the handle to a desired position. The electrosurgical handpiece may also comprise a nose piece with at least one set of circumferentially-spaced grooves, preferably two axially-spaced sets, which the surgeon can use with his fingers for one-handed orientation of the electrode position.

11 Claims, 3 Drawing Sheets

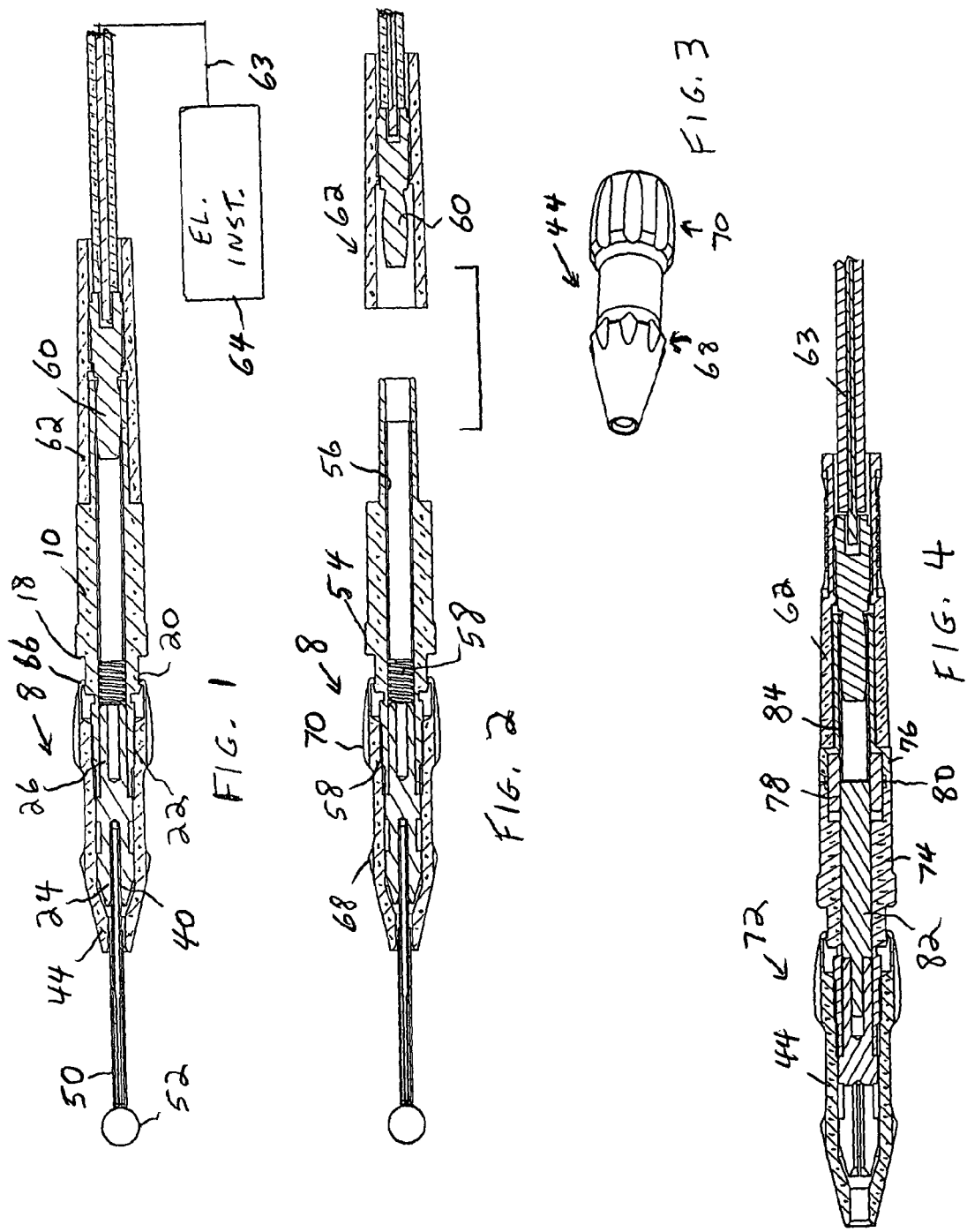

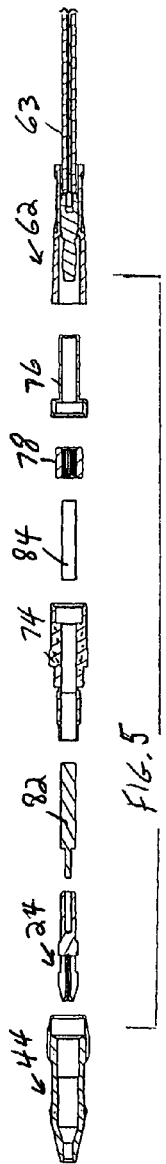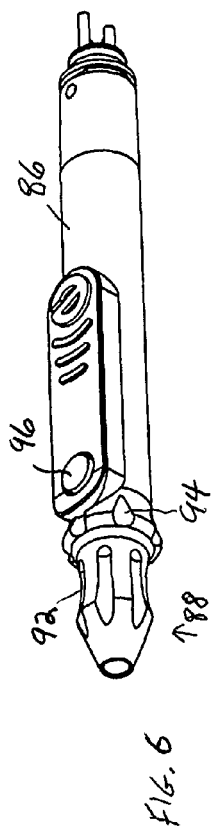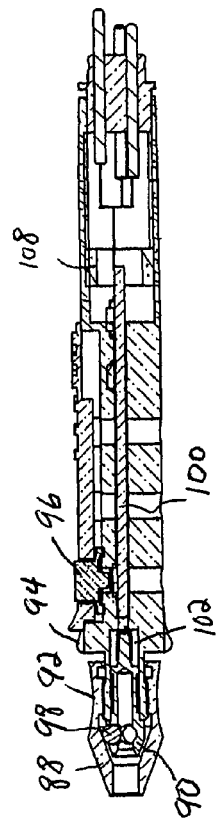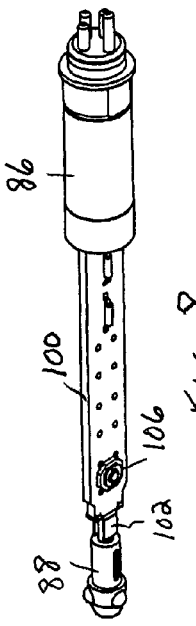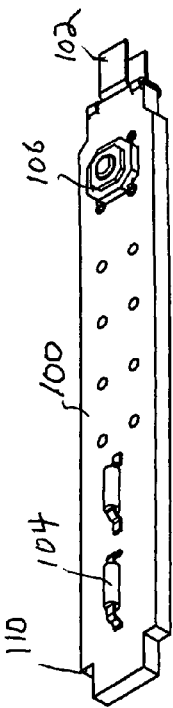

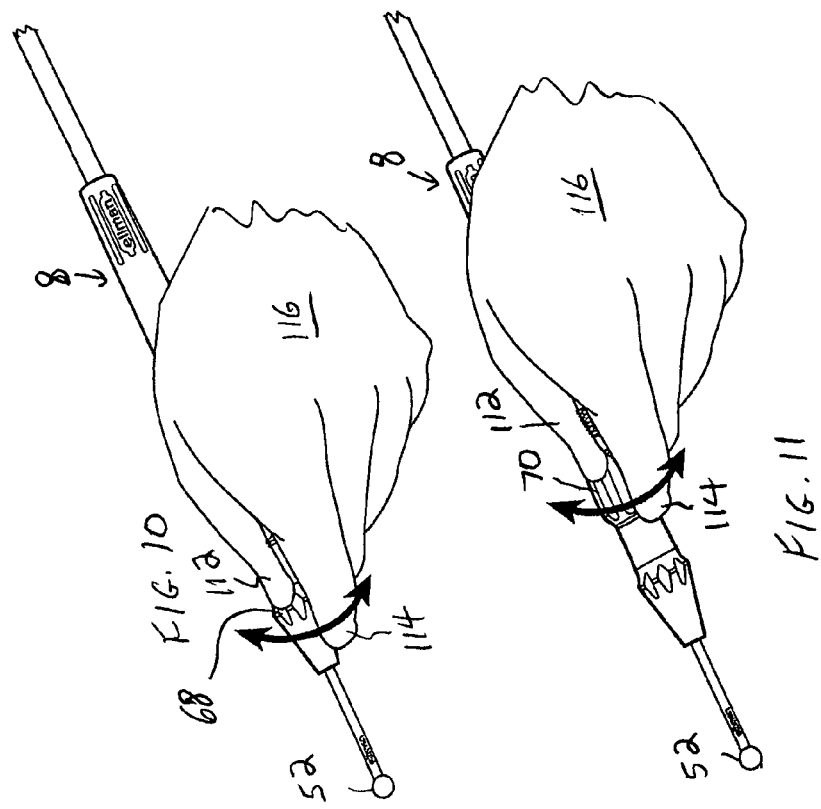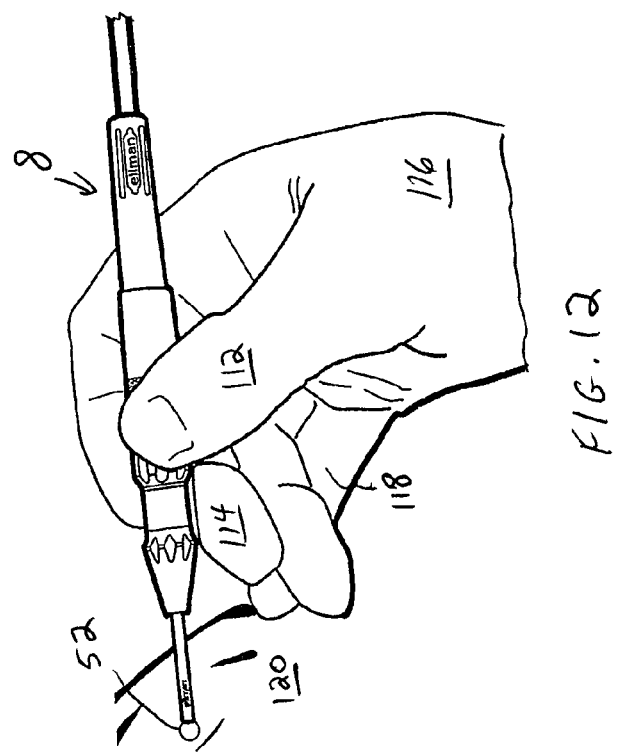

FINGER-CONTROLLABLE ELECTROSURGICAL HANDPIECE

This invention relates to a novel electrosurgical handpiece for receiving an electrosurgical electrode for use in radio-frequency (RF) electrosurgical medical, dental, and veterinarian procedures.

BACKGROUND OF THE INVENTION

Electrosurgery is a common procedure for dentists, doctors, and veterinarians. Electrosurgical unipolar handpieces are commercially available that will accommodate a wide variety of electrode shapes and sizes, such as needles, blades, scalpels, balls and wire loops. A conventional unipolar handpiece, such as that available from Ellman International, Inc. of Oceanside, N.Y., is described in U.S. Pat. No. 5,984,918, the contents of which are herein incorporated by reference, comprises an elongated electrically-insulating handle with a central bore and having at a front first end an externally threaded part for threadingly engaging an internal thread on an electrically-insulating nose piece also fitted with a central bore. A generally cylindrical metal collet seats in the handle bore at the first end and a collet front portion may project forward from the handle. The collet comprises at its front portion flexible jaws formed by a tapered slitted front with a bore sized to receive the shaft or shank of a conventional electrosurgical electrode, and the nose piece has on its interior a matching tapered portion configured such that, when the nose piece is rotated clockwise (CW) while threadingly engaged to the handle, its tapered interior surface engages and gradually closes down the collet jaws so that the electrode, when inserted into the collet bore, is tightly held by the metal collet and a good electrical connection is made to the collet. The back or second end of the collet is connected to a cable which connects to a conventional electrosurgical instrument supplying electrosurgical currents which, when activated, via a button switch on the handpiece or a foot switch or a switch on the instrument, supplies electrosurgical currents to the collet and via the collet to the electrosurgical electrode. When the dentist or doctor desires to change the shape, size or length of the electrode, it is necessary to loosen the nose piece to unlock the collet, remove the existing electrode, and substitute a new electrode.

These types of known handpieces can cause certain difficulties. These difficulties include: the handle with fingerswitches may be too long for certain procedures. A reason for this length is the presence of a circuit board inside the handle which responds to the pressing of one or more fingerswitch buttons on the handle exterior. The problem is exacerbated when three fingerswitches are provided on the handle, each connected via the circuit board to send a control signal to the electrosurgical instrument to activate a different mode of operation of the instrument. Another problem is that the surgeon may experience difficulties in positioning the active electrode end at the desired orientation at the surgical site. Also, the configuration of the handle, including the cable connection, also may interfere with the surgeon's use of the handpiece.

SUMMARY OF THE INVENTION

An object of the invention is a shorter electrosurgical handpiece that improves the surgeon's ability to control the positioning of the electrode during a procedure.

Another object of the invention is an electrosurgical handpiece specially configured to enable the surgeon to more easily position the electrode.

Still another object of the invention is an electrosurgical handpiece specially configured to enable the surgeon to comfortably hold the handpiece in several different positions and also use the same finger(s) of the handpiece-holding hand to serve as a finger rest for the hand.

Still a further object of the invention is an electrosurgical handpiece in which the cable does not interfere with the surgeon's use of the handpiece.

According to one aspect of the invention, an electrosurgical handpiece comprises a handle, a nose piece for threaded engagement with the handle at a first end, and a detachable cable connector at the opposite second end, the latter being characterized by a rotatable connection such that, when the handle is rotated by the user, the cable will tend to maintain its rotary position and thus not impede rotation of the handle to a more optimum position.

According to another aspect of the invention, the electrosurgical handpiece comprises a nose piece with at least one set of circumferentially-spaced grooves, preferably two axially-spaced sets, which the surgeon can use with his fingers for one-handed orientation of the electrode position.

According to still another aspect of the invention, the electrosurgical handpiece provided with fingerswitches and with an internal circuit board is all configured such that the overall length of the handpiece and especially the portion nearest the electrode can be significantly reduced compared to conventional handpieces.

"Press-fitted" as used herein means an interference fit wherein the outer diameter of a part such as the collet exceeds that of the handle bore by at least 0.010 inches, and preferably by at least 0.016 inches. Preferably, the collet is made of a good electrically conductive material which has sufficient elasticity that it will return to its original unstressed condition when an applied stress is removed. A preferred material for the collet is beryllium-copper which exhibits the desired elasticity, sometimes referred to as spring properties. As used herein, terms that define position are being related to the handpiece handle which possesses a longitudinal axis, and "front" means in a direction toward the electrode end of the handpiece whereas "back", "behind" or to the "rear" means in a direction away from the electrode end of the handpiece.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a cross-sectional view of one form of an electrosurgical handpiece according to the invention shown with an electrode and shown schematically connected by a cable to an electrosurgical instrument for supply of electrosurgical currents;

FIG. 2 is a cross-sectional view of the electrosurgical handpiece shown in FIG. 1 but with the cable connector detached;

FIG. 3 illustrates is a perspective view of one form of a nose piece used in the electrosurgical handpiece of the invention;

FIG. 4 is a cross-sectional view of another form of electrosurgical handpiece in accordance with the invention;

FIG. 5 is an exploded view of the electrosurgical handpiece shown in FIG. 4;

FIG. 6 illustrates in a perspective view still another form of electrosurgical handpiece of the invention characterized by a short front end;

FIG. 7 is a cross-sectional view of the electrosurgical handpiece shown in FIG. 6;

FIG. 8 is a perspective view of a sub-assembly of the FIG. 6 embodiment;

FIG. 9 is a perspective view of the circuit board assembly of the FIG. 6 embodiment;

FIG. 10 is a perspective view showing one way of using the handpiece of the invention;

FIG. 11 is a perspective view showing a second way of using the handpiece of the invention;

FIG. 12 is a perspective view showing yet another way of using the handpiece of the invention.

The figures are not to the same scale.

DETAILED DESCRIPTION OF THE PREFERRED EMBODIMENTS

FIGS. 1 and 2 show a preferred embodiment of an electrosurgical handpiece of the invention. The handpiece 8 comprises a straight, elongated, round handle 10 made, for example, of Delrin plastic, and provided with a bore. A longitudinal axis is the horizontal axis of the figures. At its left is a reduced diameter cylindrical section defined by a flanking shoulder 18 on the right and a flanking first ridge 20 on the left. The first ridge 20 is adjacent a forwardly projecting threaded portion 22.

A metal or otherwise electrically-conductive conventional collet 24 has a rear reduced-diameter cylindrical section 26 behind the collet head 24. The collet head 24 comprises at its left end jaws formed by a tapered part that has circumferentially-spaced slots extending radially from the outside to a bore 40.

A hollow nose piece is shown at 44, and comprises an electrically-insulating cylindrical member, for example, of Delrin. At its left, the nose piece 44 tapers down toward its bore. At its right end, inside of the bore is an internally threaded portion 58, matched to the threaded portion 22 on the handle. The three parts 10, 24, and 44 make up the handpiece 8. The collet bore 40 is a single coaxial section sized to accommodate, for example, a 3⁄32 inches shank; of an insulated electrode 50 shown in this instance as a conventional bare loop 52. The handle part 10 has an outer knurled surface 54. For use with a standard cable connector of the push-pull type as illustrated in our U.S. Pat. No. 6,712,813, an electrically-conductive cylinder 56 is force-fitted into the bore of the handle part 10 while compressing an internal electrically-conductive compression spring 58 against the electrically-conductive collet 24. In this example, when the banana plug end 60 of the cable connector 62 is plugged into the handpiece connector 10, as shown in FIG. 1, and the opposite end of the cable 63 plugged into a conventional electrosurgical instrument 64, then when the latter is activated, electrosurgical currents are applied to the collet and in turn to the electrode 50. The attachment of the nose piece 44 to the handle part is of the locking type described in our U.S. Pat. No. 5,630,812, in which when the nose piece 44 is tightened to grip the electrode shank 40, its right end lip 66 climbs over the ridge 20 on the handle part 10 securely attaching the nose piece to the handle.

When it is desired to remove or replace the electrode, the nose piece 44 is rotated CCW. Sufficient rotation of the nose piece 44 allows the natural elasticity of the metal of the collet jaws to relax to release the electrode which can then be withdrawn from the handpiece. What is not shown in this embodiment are the standard fingerswitches that can be added to the handpiece so that the electrode can be turned on and off by the surgeon using the handpiece switches. Also not shown is the standard footswitch which also plugs into the electrosurgical instrument 64 for operating the handpiece.

The embodiment of FIGS. 1 and 2 is characterized by the presence of two sets of grooves or notches on the nosepiece 44. The distal set 68, the set closer to the electrode, comprises eight circumferentially- and evenly-spaced short notches. The proximate set 70, the set further back from the electrode, comprises eight circumferentially- and evenly-spaced long notches.

The eight notches in each of the sets are each of the same size and each have a general oval shape whose long axis is parallel to the longitudinal axis of the handpiece. For a handpiece that has an overall length of about 4-6 inches, the rear notches 70 preferably have a depth of about 0.06-0.07 inches, and a length of about 0.56-0.76 inches. Similarly, the front notches 68 preferably have the same depth of about 0.06-0.07 inches, but a smaller length of about 0.3-0.4 inches. Thus, the two notch sets 68, 70 are distinguished: first by location, one being closer to the electrode 50 than the other; second by overall diameter, one set being on a smaller diameter section than that of the other; and third by notch length, the more distal notch set being shorter than the more proximal notch set. While eight notches per set are preferred, it is also possible for each set to have a smaller or larger number of notches, and even different numbers of notches, to provide a fourth distinction. For example, the rear set 70 can have eight notches, whereas the front set 68 can have six notches. The notches function to increase the ability of the surgeon to control the position of the electrode, explained in greater detail below.

The next embodiment illustrated in FIGS. 4 and 5 have a handpiece construction 72 similar to that of the earlier embodiment except that it addresses a problem of the latter. The problem is that a fixed connection of the cable to the handpiece sometimes encumbers the movements of the surgeon.

This problem is overcome in accordance with a feature of the invention by providing a freely rotatable connection between the cable connector 62, which is the same as before, and the handpiece connector, the rotation occurring in the handle itself. In a preferred embodiment, the handle part is divided into a front part 74 and a rear part 76. The front part 74 is basically the same as in the other embodiment. But, the rear part 76 is rotatingly mounted to the front part 74, the connection being made by a conventional needle bearing 78 (whose details are not shown as well known in the art) press-fitted inside a front handle bore and press-fitted inside a reduced diameter rear bore in the rear handle part 76. The dividing line is indicated at 80. The rotatable movement occurs inside the bearing 78. The cable end has the usual plug-in connector 62. When the cable connector 62 is plugged into the handpiece connector end 76, the front part of the handle 74 carrying the electrode 50 can now rotate freely about a fixed cable 63. In this way, the surgeon is given additional degrees of freedom to position the electrode as desired for the given procedure. The parts indicated by numerals 82 and 84 are electrically-conductive and used to convey the electrosurgical currents from the banana plug 60 to the collet 24.

The previous embodiments comprised no fingerswitches and had two sets of control notches or grooves on its nosepiece. The embodiment next to be described has an even shorter front end than the previous embodiment, has one fingerswitch, though two or more can also be provided, and while still possessing two sets of control grooves, the distal set is located on the nosepiece, but the proximal set is located on the fixed part of the handle.

FIGS. 6 and 7 illustrate different views of the same embodiment. It comprises as before a handle part 86 and a rotatable nose piece 88 housing a collet 90 for holding the electrode. In this instance, the distal groove set 92, which in this case includes the long grooves, is positioned as before on the nosepiece. But, the proximal set 94 is located at the leading edge of the handle which at that position is somewhat enlarged in diameter. The proximal groove set 94 comprises the shorter grooves, so the surgeon can distinguish by feel where his/her hand is located relative to the handpiece. The functionality is the same as in the previous embodiments. This last embodiment has a connector end of male pins for releasably engaging a female connector on the cable end.

The particular electrode 52 shown in FIG. 1 has an active or working end in the form of a wire loop. While other forms, such as needles, balls, etc., are usable, problems that are especially associated with a loop electrode arise such as that the loop, extending in a flat plane, critically needs to be oriented properly for the surgical procedure.

This problem is overcome in accordance with a feature of the invention by providing the nose piece as described with at least a first set of circumferentially-spaced notches or grooves configured such that when the handpiece is held by the surgeon with one or more of his/her fingers engaging the notches, the surgeon after a few uses quickly learns to associate a finger-notch position with the orientation of the loop electrode. Thus, the surgeon acquires improved tactile or digital control over the electrode working end. In a preferred embodiment, at least a second set of circumferentially-spaced notches, axially spaced from the first set, also is provided on the nose piece as in the FIG. 1 embodiment or on the handle part as in the FIG. 6 embodiment.

Another important feature is illustrated in a comparison of the embodiments of FIG. 6 with FIG. 4. It will be observed that the axial length of the front part of the handpiece of FIG. 6 is much shorter than that of FIG. 4. Also, observe the location of the fingerswitch 96 for activating the hand piece. It too is much closer to the electrode end of the handpiece than that of the conventional hand piece. This means that the hand of the surgeon is much closer to the electrode during use than with the conventional handpiece and he/she can still operate the fingerswitch as necessary. Most surgeons believe that they can exert better control of the electrode position the closer their hand is to the electrode.

The shorter front end is achieved in accordance with another feature of the invention by moving the proximal set of notches from the nose piece to the handle, and by reconstructing the collet to sharply reduce its length. "Collet" as used herein should be understood to mean the handpiece part that functions to grip and ungrip the electrode shank. In a preferred embodiment, the standard collet with the slitted front end is replaced by a collet 90 free of slits but housing a set of three metal balls 98 radially positioned in a plane transverse to the axis and surrounding the bore for the electrode shank. As before, when the nosepiece is rotated onto the projecting handle front end, the tapered inner surface of the nosepiece presses down on the balls 98 which in turn press down on the electrode shank to lock it into place. The reverse happens when the nosepiece is rotated CCW due to the resilience of the collet metal. The collet in this case acts as a cage for the balls. As one example, for comparison's sake, in the prior art conventional handpiece with fingerswitches, whose front end is similar to that of FIG. 1, the axial length from the tip of the nosepiece to the first fingerswitch was about 2.35 inches, whereas the axial length from the tip of the nosepiece in the FIG. 6 embodiment to the first fingerswitch 96 is about 1.38 inches, a reduction of about 40% in length.

The closer position of the fingerswitch 96 also required a reconfiguration of the handle interior to enable contact between the fingerswitch button activator on the handle top and an underlying circuit board 100. This reconfiguration is illustrated in FIGS. 7-9. The left or front end of the circuit board 100 is provided with a bifurcated spring clip 102 (note that the view in FIG. 9 is reversed for clarity). On the circuit board 100 are mounted several resistors and a switch 106 to be activated by the handle button 96. An elastomeric sleeve 108 mounted inside the handle rear seats in a recessed area 110 at the rear end of the circuit board 100 (the reversed left side in FIG. 9), and urges the circuit board 100 and its spring clips 102 at the front end against the back end of the collet inside the nose piece 88 (shown in FIG. 8) to maintain the assembly in place and ensure proper electrical connections to the electrode.

The way in which the notch sets can be used by the surgeon is illustrated in FIGS. 10-12 using the handpiece of FIG. 1 as an example. FIG. 11 shows a first way in which the surgeon can hold the handpiece for use during a procedure. In this first way, the handpiece is held such that the thumb 112 and forefinger 114, primarily the thumb, of the hand 116 is positioned on the second or distal set of notches 70. The double-ended arrow indicates that the surgeon can rotate the handpiece using just the thumb and finger. In this first instance, the surgeon's hand though further from the electrode 52 still can exercise more control over the position of the wire loop electrode 52 than with the prior art handpiece.

FIG. 10 shows a second way in which the surgeon can hold the handpiece for use during a procedure. In this second way, the handpiece is held such that the thumb 112 and forefinger 114, primarily the thumb, is positioned on the first or proximal set of notches 68. The double-ended arrow indicates that the surgeon can rotate the handpiece using again just the thumb and finger. In this second instance, the surgeon's hand 116 is closest to the electrode and thus the surgeon has the closest control over the position of the wire loop electrode 52.

FIG. 12 shows still another way to hold the handpiece where very close control is desired over the depth of the incision, using other parts of the hand as a rest position for the electrode. In many procedures, the loop electrode is used to excise a growth or similar lesion, and in such case it is important to avoid cutting too deeply into healthy tissue. In this instance, the surgeon can rest one or more of his other fingers 118 on the same hand that holds the handpiece on the tissue surface 120 adjacent the surgical site, which gives him/her even greater control over the position of the electrode working end with respect to the tissue being excised.

While the handpiece of FIGS. 1-3 lacks fingerswitches, FIG. 6 shows an embodiment in accordance with the invention with one button fingerswitch. The fingerswitches as is well known can be used by the surgeon to activate different modes of the electrosurgical instrument, and when three are present, the modes typically are CUT, CUT/COAG, or HEMO mode. For optimum performance, the electrosurgical instrument should operate to produce RF electrosurgical currents at about 4 MHz.

As described above, the collet 24 must be constituted of an electrically conductive metal that has a certain amount of elasticity or spring force, meaning that, when a stress is removed, it will tend to return to its original dimensions. This property also allows it to be force fitted into the handle bore without breaking the plastic body. Beryllium-copper is well suited as the collet material for this purpose. Other plastics with similar properties to the Delrin may also be suitable, but the latter is preferred because it has a certain degree of softness, which simplifies assembly of the product.

The advantages of the RF handpiece of the invention include:
- shorter radius from the finger grip to the tip of the RF electrode;
- more accurate performance due to less surgeon concentration required to position the electrode when it is fixed in the handpiece chuck;
- quick cable access can also rotate, and cable is easily changed if damaged and easily changed from instrument to instrument due to the quick disconnect cable;
- less thermal damage to the patient due to the firmer tactical control and closer location of the fingers which provide better digital dexterity;
- the shorter design and closer positioning of the hand and fingers offers better control of hand shaking during surgical procedures especially delicate surgery;
- grooved finger rests provide firm accurate control.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical handpiece for use by a surgeon comprising:
   an elongated handle member having a longitudinal axis and having at a first end a first portion for receiving and holding a nose piece and a second end,
   first means for removably receiving and holding an electrode, said first means being positioned on the handle member at its first end under the nose piece such that when an electrode is mounted on and gripped by the first means the gripped part projects generally parallel to the longitudinal axis in a direction frontward of the handle member,
   an electrode connector at the second end and connected to the first means,
   the nose piece having a second portion for engagement with the first portion and configured such that, when rotated while in engagement with the first portion of the handle member, the nose piece functions to cause the first means to tighten and to loosen its grip on the electrode,
   the nose piece having on its outer surface at a position close to the first end at least a first set of longitudinally-extending circumferentially-spaced notches, the notches being circumferentially spaced by non-notched areas such that when the handle member is held by the surgeon with a finger or fingers of the surgeon engaging one or more of the notches and the non-notched areas, the surgeon acquires improved tactile control over the electrode,
   the nose piece comprising on its outer surface a second set of circumferentially-spaced notches axially spaced by non-notched areas from the first set and further removed from the first end.

2. An electrosurgical handpiece as claimed in claim 1, wherein the first set of nose piece notches comprises notches of a given axial length and the second set of nose piece notches comprises notches whose axial length is different from that of the first set.

3. An electrosurgical handpiece as claimed in claim 2, wherein the first and second set of nose piece notches each total about 8 notches.

4. An electrosurgical handpiece as claimed in claim 2, wherein each of the notches of the first and second sets extend generally longitudinally and are generally oval shaped.

5. In combination, the electrosurgical handpiece as claimed in claim 1 and an electrosurgical instrument producing RF electrosurgical currents of about 4 MHz, the former being plugged into the latter.

6. An electrosurgical handpiece for use by a surgeon comprising:
   an elongated handle member having a longitudinal axis and having at a first end a first portion for receiving and holding a nose piece and a second end,
   first means for removably receiving and holding an electrode, said first means being positioned on the handle member at its first end under the nose piece such that when an electrode is mounted on and gripped by the first means the gripped part projects generally parallel to the longitudinal axis in a direction frontward of the handle member,
   an electrode connector at the second end and connected to the first means,
   the nose piece having a second portion for engagement with the first portion and configured such that, when rotated while in engagement with the first portion of the handle member, the nose piece functions to cause the first means to tighten and to loosen its grip on the electrode,
   the nose piece comprising axially-spaced larger-diameter sections separated by a smaller-diameter section,
   the nose piece having on its outer surface at a position close to the first end at least a first set of longitudinally-extending circumferentially-spaced notches, the notches being circumferentially spaced by non-notched areas such that when the handle member is held by the surgeon with a finger or fingers of the surgeon engaging one or more of the notches and the non-notched areas, the surgeon acquires improved tactile control over the electrode,
   the nose piece further comprising on its outer surface a second set of circumferentially-spaced notches axially spaced from the first set and further removed from the first end,
   the first notch set being on one of the larger sections, the second notch set being on the other of the larger sections.

7. An electrosurgical handpiece for use by a surgeon comprising:
   an elongated handle member having a longitudinal axis and having at a first end a first portion for receiving and holding a short nose piece and a second end,
   first means for removably receiving and holding an electrode, said first means being positioned on the handle member at its first end under the nose piece such that when an electrode is mounted on and gripped by the first means the gripped part projects generally parallel to the longitudinal axis in a direction frontward of the handle member,
   an electrode connector at the second end and connected to the first means,
   the nose piece having a second portion for engagement with the first portion and configured such that, when rotated while in engagement with the first portion of the handle member, the nose piece functions to cause the first means to tighten and to loosen its grip on the electrode, the nose piece having on its outer surface a first set of circumferentially-spaced notches, the part of the handle member adjacent the nose piece comprises on its outer surface a second set of circumferentially-spaced notches axially spaced by non-notched areas from the first set, each of the notches of the first and second set of notches being circumferentially-spaced by non-notched areas such that when the handle member is held by the surgeon with a finger or fingers of the surgeon engaging one or more of the notches and the non-notched areas, the surgeon acquires improved tactile control over the electrode.

8. An electrosurgical handpiece as claimed in claim 7, wherein the first and second notch sets are composed of oval-shaped notches having different lengths and are positioned on parts of the handpiece having different diameters.

9. An electrosurgical handpiece as claimed in claim 7, wherein the first means comprises a collet in the form of radially positioned balls supported by a ball cage with the balls in contact with the first means.

10. An electrosurgical handpiece as claimed in claim 7, further comprising a button fingerswitch on the handle adjacent the part of the handle member containing the second notch set, and a circuit board inside the handle positioned to be contacted by the button when the latter is pressed.

11. An electrosurgical handpiece as claimed in claim 10, wherein the circuit board comprises a bifurcated spring clip contacting the first means.

* * * * *